(12) United States Patent
Stephan

(10) Patent No.: US 9,387,506 B2
(45) Date of Patent: Jul. 12, 2016

(54) PROCESS FOR PREPARING A CERAMIC BODY HAVING A SURFACE ROUGHNESS

(71) Applicant: Straumann Holding AG, Basel (CH)

(72) Inventor: Marc Stephan, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 14/560,230

(22) Filed: Dec. 4, 2014

(65) Prior Publication Data

US 2015/0087492 A1 Mar. 26, 2015

Related U.S. Application Data

(63) Continuation of application No. 13/504,596, filed as application No. PCT/EP2010/006615 on Oct. 29, 2010, now Pat. No. 8,920,868.

(30) Foreign Application Priority Data

Nov. 2, 2009 (EP) .................................... 09013742

(51) Int. Cl.

| | |
|---|---|
| *B05D 1/12* | (2006.01) |
| *A61C 8/00* | (2006.01) |
| *A61C 13/00* | (2006.01) |
| *A61L 27/04* | (2006.01) |
| *C04B 41/87* | (2006.01) |
| *C04B 41/00* | (2006.01) |
| *C04B 41/50* | (2006.01) |
| *C04B 35/48* | (2006.01) |
| *C04B 35/64* | (2006.01) |
| *C04B 35/645* | (2006.01) |
| *C04B 35/486* | (2006.01) |
| *C23C 24/04* | (2006.01) |
| *A61F 2/30* | (2006.01) |
| *C04B 111/00* | (2006.01) |

(52) U.S. Cl.
CPC ............... *B05D 1/12* (2013.01); *A61C 8/0012* (2013.01); *A61C 13/0007* (2013.01); *A61L 27/047* (2013.01); *C04B 35/48* (2013.01); *C04B 35/486* (2013.01); *C04B 35/64* (2013.01); *C04B 35/6455* (2013.01); *C04B 41/009* (2013.01); *C04B 41/5042* (2013.01); *C04B 41/87* (2013.01); *A61F 2/30767* (2013.01); *A61F 2310/00179* (2013.01); *A61F 2310/00634* (2013.01); *A61L 2400/18* (2013.01); *C04B 2111/00836* (2013.01); *C04B 2235/604* (2013.01); *C04B 2235/608* (2013.01); *C04B 2235/6562* (2013.01); *C04B 2235/6565* (2013.01); *C04B 2235/77* (2013.01); *C04B 2235/963* (2013.01); *C23C 24/04* (2013.01)

(58) Field of Classification Search
CPC .................................. B05D 7/00; C23C 24/04
USPC ................. 427/2.24, 456, 457, 532; 106/1.05
See application file for complete search history.

(56) References Cited

U.S. PATENT DOCUMENTS

| | | | | |
|---|---|---|---|---|
| 6,030,472 | A | * 2/2000 | Hajaligol | .................. B22F 3/18 148/651 |
| 2003/0044624 | A1 | * 3/2003 | Spitsberg | .............. C23C 28/321 428/469 |
| 2007/0240603 | A1 | * 10/2007 | Ko | ............................ C23C 4/12 106/1.05 |

FOREIGN PATENT DOCUMENTS

DE 102006062712 * 8/2007 .............. C23C 24/04

*Primary Examiner* — Andrew Bowman
(74) *Attorney, Agent, or Firm* — Oliff PLC

(57) ABSTRACT

A process for preparing a ceramic body having a surface roughness, said process comprising the step of depositing particles of a ceramic material on the surface of a ceramic basic body. The process is characterized in that separate agglomerates comprising at least two particles and a binder binding the particles together are deposited on the surface of the basic body by projecting the agglomerates towards the basic body.

20 Claims, 6 Drawing Sheets

PROCESS FOR PREPARING A CERAMIC BODY HAVING A SURFACE ROUGHNESS

FIELD OF THE INVENTION

The present invention relates to a process for preparing a ceramic body having a surface roughness, to a ceramic body obtainable by this process, and to the use of the ceramic body as an implant, in particular a dental implant.

BACKGROUND

Implants, such as dental implants, are well known in the art. They generally consist of a material, which is biocompatible and which additionally has a low elastic modulus and a high strength.

Apart from its biocompatibility and its mechanical properties, the osteointegrative properties of an implant are usually of major importance. The term osteointegration designates the direct structural and functional connection between living bone and the surface of the load-bearing implant. A good osteointegration means that the implant, after reaching a primary stability by screwing it into the bone, safely ossifies within a short healing time so that a permanent bond between implant and bone is obtained.

Dental implants which are currently in use are in general made of a metal, e.g. titanium, or a ceramic, e.g. a zirconia based ceramic, due to the biocompatibility and the favourable mechanical properties of these materials.

In contrast to titanium implants, which are dark and therefore mismatch with the color of natural teeth, ceramic materials have the advantage that their color can be closely matched to the natural tooth color. Efforts have thus been made to provide dental implants, of which at least the parts that are visible after insertion are made of a ceramic material.

Despite their favourable properties with regard to the color, the use of ceramic materials for dental implants is in many cases limited by their fatigue stability, which is generally rather low.

A ceramic material having a high mechanical strength is disclosed in U.S. Pat. No. 6,165,925, which relates to an yttrium-stabilized zirconium oxide in predominantly tetragonal form for the production of a sintered semi-finished article.

In order to achieve a sufficient mechanical stability, the zirconia ceramic disclosed in U.S. Pat. No. 6,165,925 must be highly dense. The surface of such a highly dense zirconia ceramic is clean cut, extremely hard and has essentially no porosity. A dental implant made of such a zirconia ceramic is thus bio-inert and has only weak osteointegrative properties.

For providing an osteointegrative ceramic surface, a variety of different techniques have been suggested:

WO-A-2005/027771 relates to a process for preparing a dental installation in which a dispersion is applied on a substrate having a first porosity, said dispersion forming upon sintering a ceramic layer with a second porosity.

EP-A-0870478 relates to a dental retention element having a core of a high-strength material such as zirconia, said core being coated with a ceramic material which can be chemically and/or mechanically processed.

The composite structures disclosed in WO-A-2005/027771 and EP-A-0870478 have the disadvantage that the ceramic coating is easily chipped off.

Alternatively, a treatment comprising abrasive blasting and acid-etching for providing osteointegrative properties to the ceramic implant's surface has been suggested by EP-B-1450722 and EP-A-1982670.

EP-B-1450722 relates to a dental implant made of zirconia ceramic which after abrasive blasting is subjected to a treatment using phosphoric acid, sulphuric acid, hydrochloric acid or mixtures thereof.

EP-A-1982670 relates to a process wherein a roughness is provided to the surface of the dental implant by sandblasting, milling and/or injection molding techniques prior to the etching of the implant with an etching solution comprising hydrofluoric acid.

Although the process disclosed in EP-A-1982670 leads to an implant having excellent osteointegrative properties, the techniques applied prior to the etching have several disadvantages.

The sandblasting, for example, goes along with a loss of material due to the fact that it is an erosive technique. In particular with regard to ceramic implants, the relatively harsh treatment of the surface might result in the formation of defects and a phase transformation of the tetragonal to the monoclinic zirconia phase and thus in a negative impact on the mechanical stability of the implant.

Providing a structure by milling or injection molding techniques, which are mentioned in EP-A-1982670 as alternatives to the sandblasting, is relatively complicated and thus expensive. In particular, the injection molding techniques require sophisticated approaches for example with regard to the removal from the mold.

A further alternative technique for providing a structure to the surface of a ceramic implant is described in DE-A-102006062712, which relates to a process in which the surface roughness is increased prior to the sintering by applying sharp-edged particles to the surface of the so-called green body and/or brown body. It is thereby preferred that the green body and/or the brown body is coated with a binder for fixation of the particles.

According to another embodiment of the technique described in DE-A-102006062712, the particles are mixed with the binder and applied on the green body and/or the brown body.

DE-A-102006062712 thus teaches single particles to be applied on the surface of the implant body, which leads to protrusions in the shape of the particles. As mentioned above, it is according to DE-A-1020060621712 essential that these particles are sharped-edged.

In order to prevent the implant to be damaged, DE-A-1020060621712 teaches that the particles are "trickled" on the green body and/or the brown body, respectively, without exerting pressure ("drucklos"). As illustratively shown in DE-A-1020060621712, a body with an interface between a basic body and the applied particles is thereby obtained.

The process according to DE-A-1020060621712 is however relatively complicated to perform. In particular with regard to the particles being trickled without exerting pressure, they tend to fall off the surface on which they are applied. Also, due to the fact that the trickled particles tend to accumulate in the valleys of the surface topography rather than on the peaks, a homogenous distribution of the particles is difficult to obtain.

SUMMARY OF THE INVENTION

The object of the present invention is thus to provide a process for preparing a ceramic body having a homogenous surface roughness, said process being easy to perform and leading to a surface having increased osteointegrative properties.

According to one embodiment, the process of the present invention comprises the step of depositing particles of a ceramic material on the surface of a ceramic basic body. Thereby, separate agglomerates comprising at least two particles and a binder binding the particles together are deposited on the surface of the basic body by projecting the agglomerates towards the basic body. In contrast to the teaching of DE-A-1020060621712, no single particles are thus deposited on the surface, which is essential for achieving sharped-edged protrusions, but agglomerates of particles.

Due to the fact that agglomerates are projected towards the surface of the basic body, completely different structures are formed than according to DE-A-DE-A-1020060621712. These structures can be explained by the analogy of snowballs, for example, which are projected towards a wall, as shown in the following:

Given that the agglomerates according to the present invention generally deform like snowballs when impacting on the basic body, the contact area between the agglomerate and the basic body is augmented, thus leading to a good fixation of the deposited material. The deposited agglomerates roughly have the shape of elevations having a relatively large base area and tapering to a rounded apex.

As a further contrast to what is described in DE 1020060621712, the present invention allows an implant to be obtained which in the area near its surface has a density that gradually decreases in direction to the surface. There is thus no discrete interface on which separate particles are applied on, as according to DE-A-1020060621712. Accordingly, the problems of particles falling off the interface can be circumvented by the present invention.

Using agglomerates of particles instead of discrete particles, the present invention allows a homogenous surface roughness to be obtained in a very simple manner.

As mentioned above, this is not the case for the method according to DE-A-1020060621712. Applying the above mentioned snowball analogy, the trickling of separate particles taught by DE-A-1020060621712 would correspond to the trickling of snowflakes which also tend to accumulate in the valleys of a topography rather than on the peaks and are thus not distributed homogenously.

It has been found that the roughness obtained according to the present invention has excellent osteointegrative properties. Depending on the specific desired osteointegrative properties, the roughness can further be adapted by subsequent etching, in particular with an etching solution comprising hydrofluoric acid according to the process described in EP-A-1982670 and corresponding US2008/261178 published Oct. 23, 2008, U.S. Ser. No. 12/105,595 filed Apr. 18, 2008 entitled Process for Providing a Topography to the Surface of a Dental Implant, by Homann et al., the disclosure of which is incorporated herein by reference.

In contrast to the teaching of DE-A-1020060621712, which teaches the "trickling" of particles without exerting pressure, the agglomerates according to the present invention are preferably projected towards the basic body by means of a carrier gas stream. As a rule, the carrier gas is inert with respect to the agglomerates and, preferably, is air. The use of a carrier gas stream allows the solid particles agglomerates to be accelerated in a manner such that when impacting on the basic body, deformation of the agglomerates is accomplished, leading to the above described elevations.

According to a preferred embodiment of the present invention, the breaking load (or breaking force) of the agglomerates to be projected is in the range of 1 to 7 mN, preferably 2 to 6 mN, more preferably 3 to 5 mN. It is in this regard further preferred that the mean specific breaking strength of the agglomerates to be projected is in the range of 0.4 to 1.5 MPa, preferably 0.5 to 1.4 MPa, more preferably 0.6 to 1.3 MPa, and most preferably 0.8 to 1.2 MPa.

In practice, the breaking load values are determined by continuously measuring the force exerted on a single agglomerate by a ram as a function of the ram's displacement. Based on the measured breaking load $F_b$ (i.e. the point in the force/displacement curve, from which on the exerted force for a given displacement decreases) and the diameter of the agglomerate, the specific breaking strength $\sigma$(sigma) can be determined according to the following equation: $\sigma(sigma)=4 \cdot F_b/(\pi(pi) \cdot d^2)$. The preferred breaking load and mean specific breaking strength values given above particularly apply to agglomerates having a diameter of about 80 μm (micrometer).

By using agglomerates having the above described breaking load and specific breaking strength values, the surface of the basic body is on the one hand not damaged even when using a carrier gas stream having a relatively high flow rate. On the other hand, the "spreading" of particles of the impacting agglomerates is such that the above described elevations are formed on the ceramic body's surface which ultimately leads to a preferred surface topography.

According to a further preferred embodiment, the agglomerates have an average diameter ranging from 20 μm (micrometer) to 100 μm (micrometer), preferably from 50 μm (micrometer) to 70 μm (micrometer), leading to a surface having particularly high osteointegrative properties.

Given the fact that the grain size of the ceramic particles is typically around 30 nm to 70 nm, for example about 360 Å (36 nm) when using zirconia powder of the grade TZ-3YSB-E (Tosoh Corporation), the number of particles comprised by an agglomerate is in general in the range of several millions or billions.

According to another preferred embodiment, the ceramic material of the particles is identical to the ceramic material of the ceramic basic body, thus leading to a fully homogenous ceramic body. Alternatively, any other ceramic material which is compatible with the material of the basic body can be deposited.

The binder can for example be a polyvinyl alcohol (PVA). Alternatively, any other binder which is suitable for the purpose of the present invention can be used.

It has been found that the above mentioned preferred breaking load and specific breaking strength values can be achieved by an agglomerate which further comprises polyethylene glycol (PEG) and by suitably setting the ratio of PVA to PEG. In particular, the amount of PVA can range from about 0.1 to 3.6 wt-% and the amount of PEG can range from about 0.5 to 4.0 wt-%. The weight ratio of PVA to PEG thus typically ranges from about 7:1 to about 1:40. Preferably, the weight ratio of PVA to PEG ranges from about 1:1.4 to 1:5.

Since the material of the ceramic basic body typically comprises a pressing agent, it is preferred that the agglomerates also comprise a pressing agent in order to arrive at a fully homogenous ceramic body.

Given the fact that according to the present invention agglomerates instead of single particles are projected towards the basic body, a sand-blasting apparatus can be used. The projection by a sand-blasting apparatus is particularly preferred, since it allows the parameters, such as the amount of material to be deposited, the blasting pressure, the blasting distance and the blasting duration, to be adapted to the respective needs. In particular, the parameters can be chosen in a manner such that the momentum of the agglomerates is high enough to ensure a good fixation of the agglomerates on the basic body's surface, but low enough to prevent damages on the surface.

The structure of the surface topography to be provided can in particular be controlled by adapting the blasting distance and thus the blasting cone.

If needed, the sand-blasting apparatus can further comprise means for cooling in order to prevent a melting of the organic fraction of the agglomerate at the blasting nozzle.

In general, the ceramic body is prepared by a sintering process. Respective sintering processes are known to the person skilled in the art and for example described in WO 2005/115268, and corresponding US2005/261795 published Nov. 24, 2005, U.S. Ser. No. 10/851,911 filed May 21, 2004 entitled Method of Making Ceramic Dental Restorations, by Ghosh et al., the disclosure of which is incorporated herein by reference.

With regard to the sintering, the process of the present invention preferably further comprises the steps of
 a. forming a green basic body comprising particles of a ceramic material and a binder, said ceramic material and said binder being independently from each other different or identical to the ceramic material and the binder, respectively, of the agglomerate,
 b. forming a brown basic body by removing the binder from the green basic body, and
 c. forming the ceramic body by sintering the brown basic body.

It is thereby preferred that the agglomerates are deposited on the surface of the green basic body. This is due to the fact that the green basic body comprising the binder generally withstands the momentum of the agglomerates better than the brown basic body. Also, since according to this embodiment the basic body and the agglomerates deposited thereon are sintered in the same step, no cracks are formed which might arise due to the shrinkage of the material during sintering.

Preferably, the composition of the agglomerates is identical to the composition of the green basic body. Typically, the green basic body is formed by pressing the granulated material which also corresponds to the agglomerates according to the present invention.

A ceramic body having particularly preferred mechanical properties is obtained when the ceramic basic body and/or the agglomerates comprise particles of yttria-stabilized zirconia. In general, an yttria-stabilized zirconia according to ISO 13356 is used. An example of a preferable yttria-stabilized zirconia is Tosoh zirconia powder of grade TZ-3YSB-E (Tosoh Corporation) comprising 4.95 to 5.35 wt-% $Y_2O_3$, 0.15 to 0.35 wt-% $Al_2O_3$, at most 0.02 wt-% $SiO_2$, at most 0.01 wt-% $Fe_2O_3$, at most 0.04 wt-% $Na_2O$ and comprising a binder in an amount corresponding to an Ig-loss of 2.7 to 3.9 wt-%, the percentages being based on the total weight of the zirconia powder.

According to a preferred embodiment, the process further comprises the subsequent step of
 d. thermal post-processing, in particular hot isostatic pressing (HIP), of the ceramic body.

In general, the hot isostatic pressing includes—after treatment of the ceramic body in an inert pressurizing gas—the treatment of the body in air.

According to a further aspect, the present invention relates to a ceramic body obtainable by the process described above.

Due its high osteointegrative properties, the ceramic body obtainable by the above process is preferably used as an implant, more preferably as a dental implant.

BRIEF DESCRIPTION OF THE DRAWINGS

The invention is further illustrated by way of the attached figures, of which.

DETAILED DESCRIPTION

Figure 1:
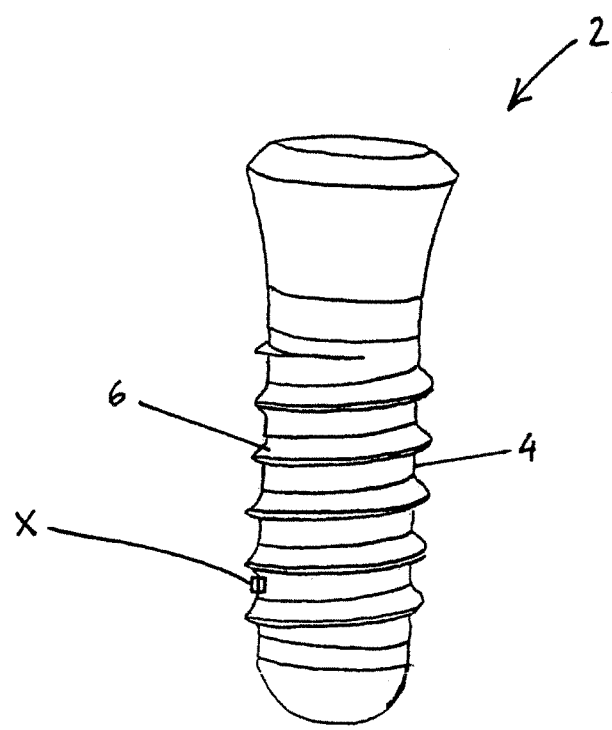
FIG. 1 is a perspective view of a ceramic body according to the present invention in the form of a dental implant.

As can be seen from FIG. 1, the dental implant 2 comprises a bone contact surface 4 intended to be embedded into the bone and comprising a threaded portion 6.

In order to allow for a good primary stability of the dental implant after implantation, at least the bone contact surface 4 is provided with a surface roughness according to the present invention.

Figure 2:
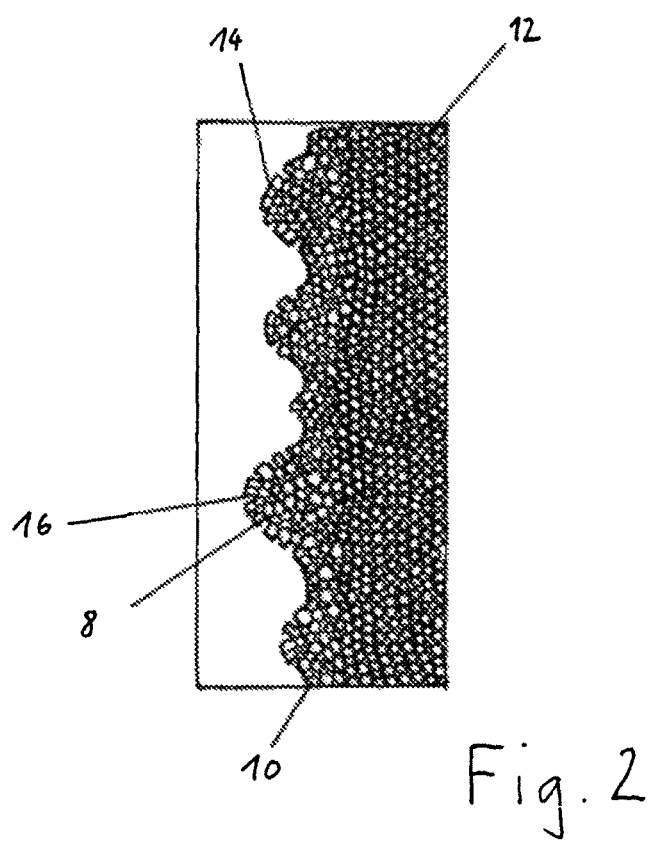
FIG. 2 shows schematically a cross-sectional view of sector X of FIG. 1.
Figure 3:
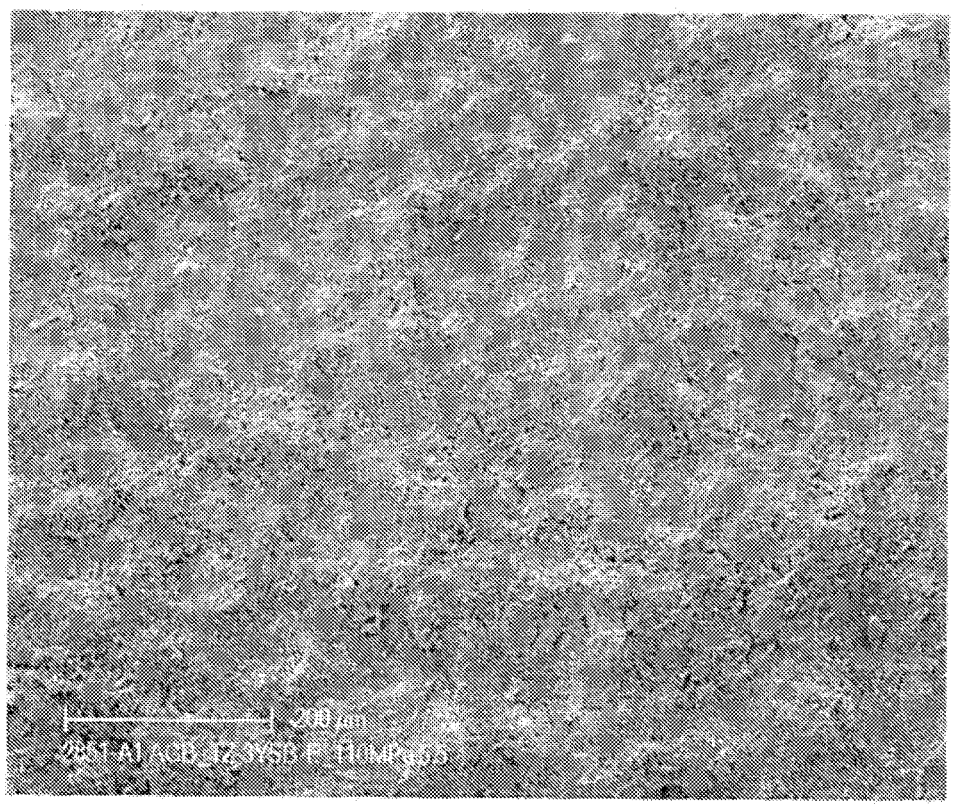
FIG. 3 shows a scanning electro-micrograph of a portion of the surface of a ceramic body obtained according to example 1, the scaling given in the micrograph corresponding to 200 μm (micrometers)
Figure 4:
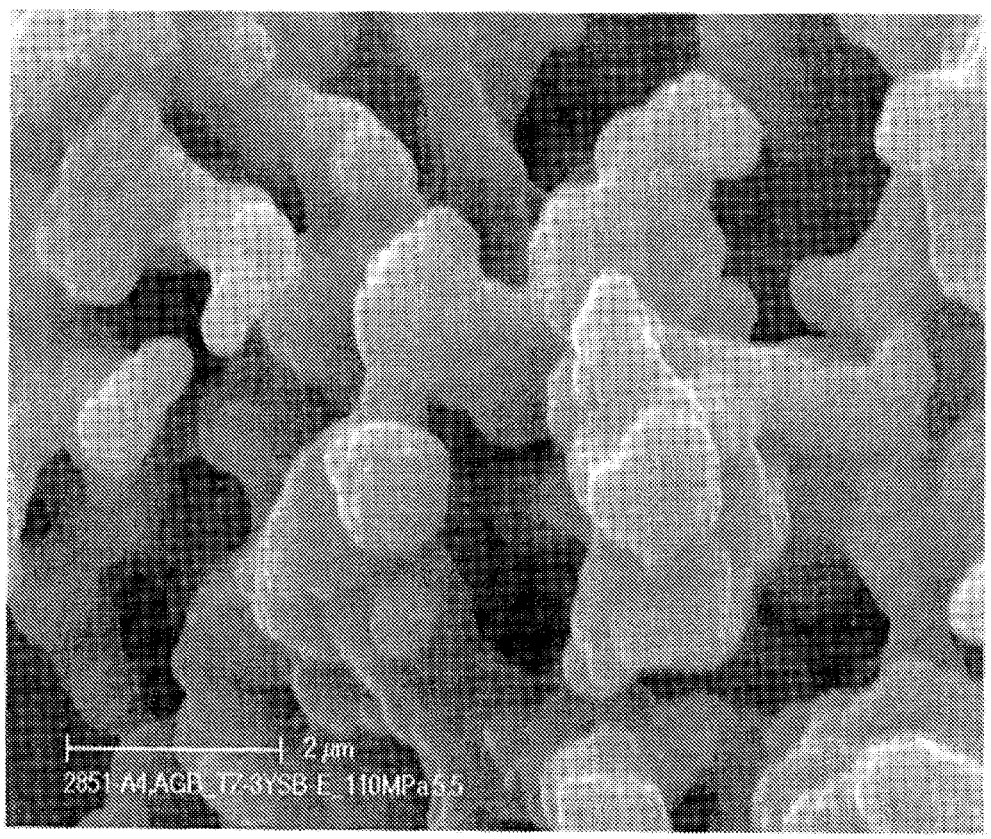
FIG. 4 shows the magnification of the scanning electro-micrograph given in FIG. 3, the scaling given in the micrograph corresponding to 2 μm (micrometers)

As given in FIG. 2, the surface roughness is formed by agglomerates 8 comprising particles 10, said agglomerates 8 being projected toward a basic body 12. When impacting on the basic body 12, the agglomerates 8 are deformed, thus resulting in a "macroroughness" which can be described by the above mentioned snowball-analogy. Due to the specific process of the present invention, there is no discrete interface between the basic body 12 and the particles 10 applied, but a density gradient that continuously decreases in direction to the surface 14. This continuous decrease of the density goes along with an increase of the porosity, leading to cavities 16 in the surface 14 forming a "microroughness".

The invention is more specifically described by the following examples:

EXAMPLES

Example 1

About 5 g of a zirconia powder of the grade TZ-3YSB-E (Tosoh Corporation) defined above, the crystallites having a grain size of about 360 Å has been pressed by a double-acting powder compressing tool (Fa. Paul-Otto Weber Maschinen- and Apparatebau GmbH; Model 20; size II, diameter 20 mm) using a press (Zwick Universalprüfmaschine) with a pressing force of about 110 MPa (about 34.5 kN). Thereby, green basic bodies having a density of about 2.8 g/cm³ are obtained.

Regarding the grain size of the crystallites, higher values up to about 700 Å (70 nm) are also thinkable.

The zirconia powder, which also corresponds to the agglomerates of the present invention, was loaded into a sandblasting-apparatus (Renfert Basic Quattro) and projected towards the green basic body for about 2 to 3 seconds under a blasting pressure of about 5.5 bar and at a blasting distance of about 14 cm.

The green bodies comprising the agglomerates applied thereon were then treated in a high-temperature kiln (Mihm-Vogt-Hochtemperaturofen HT) in accordance with the following program:

a) heating at a heating rate of 1° C./min to 600° C. and maintaining the temperature at 600° C. for 2 hours to obtain a brown body;
b) heating at a heating rate of 5° C./min to 1450° C. and maintaining the temperature at 1450° C. for 2 hours to obtain a fully sintered (white) body;
c) cooling at a cooling rate of 10° C./min down to 1000° C. and then cooling naturally from 1000° C. to room temperature.

After sintering, the samples have a density of about 6.07 g/cm$^3$.

Example 2

In analogy to the example described above, the process of the present invention has been carried out by projecting the agglomerates towards a sintered basic body instead of the green basic body.

The results of Examples 1 and 2 are shown in FIGS. 3 to 4 and 5 to 6, respectively.

As is apparent from the these figures, a surface roughness having relatively smooth peaks and valleys is obtained according to the present invention, which is in contrast to the sharped-edged structures aimed for according to DE-A-1020060621712. Illustratively, the surface topography can be described by the analogy of snowballs, which are projected towards a wall.

Figure 5:
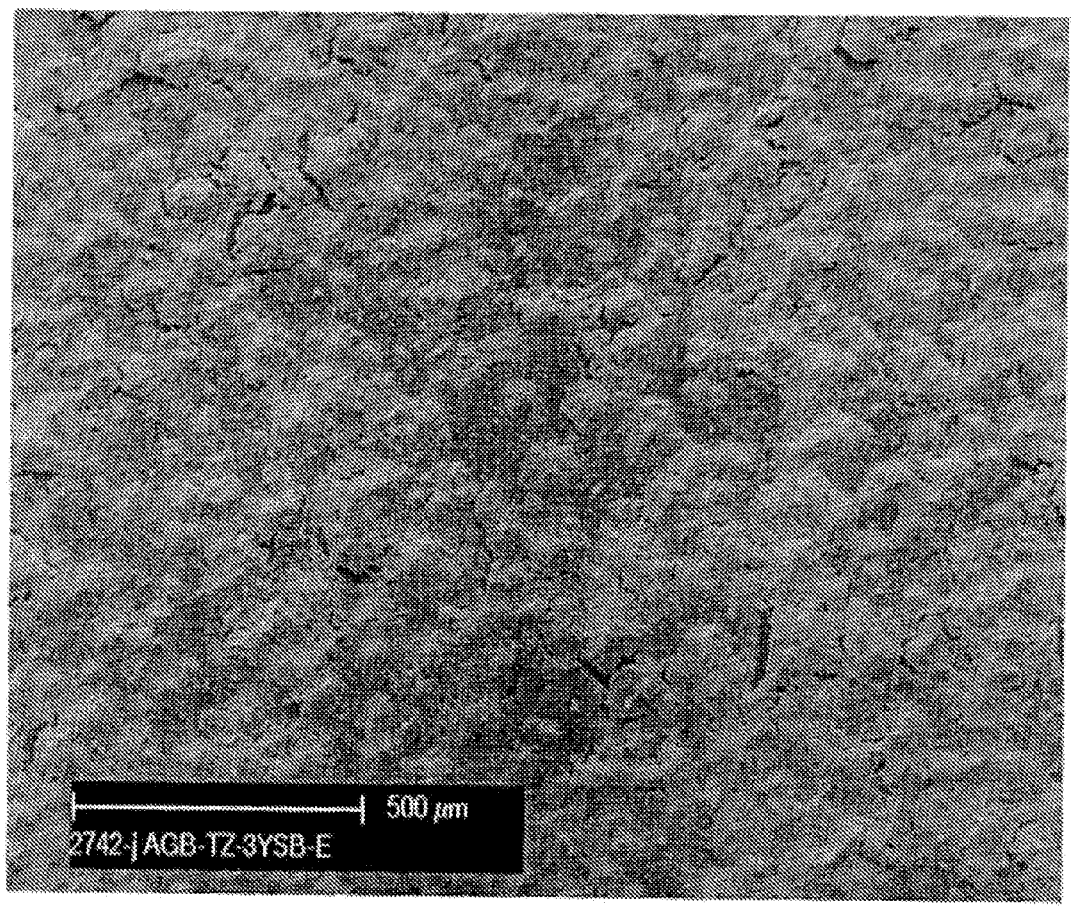
FIG. 5 shows a scanning electro-micrograph of a portion of the surface of a ceramic body obtained according to example 2, the scaling given in the micrograph corresponding to 200 μm (micrometers)
Figure 6:
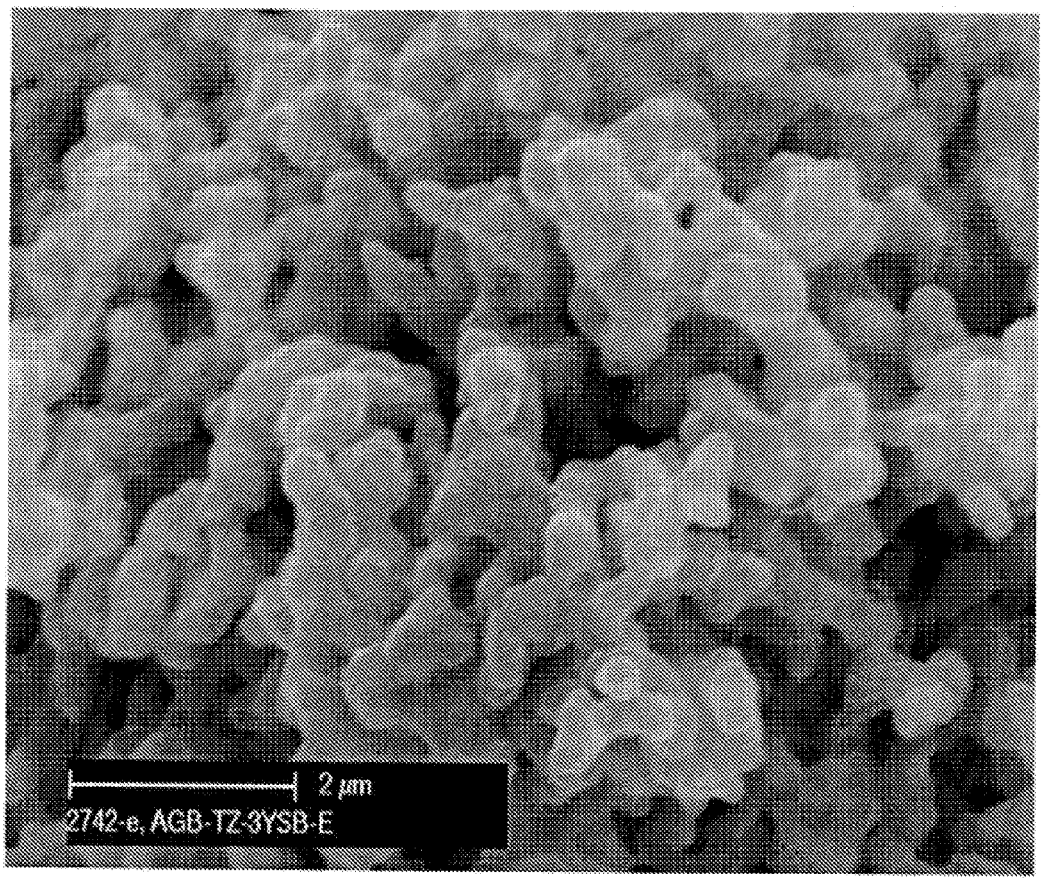
FIG. 6 shows the magnification of the scanning electro-micrograph given in FIG. 5, the scaling given in the micrograph corresponding to 2 μm (micrometers).

As shown in FIG. 5, the surface obtained according to Example 2, i.e. by projecting the agglomerates towards an already sintered basic body, can comprise cracks. Without any intention of being bound by the theory, it is assumed that these cracks are formed due to the shrinkage of the deposited material during sintering it, which in Example 2 is not compensated by shrinkage of the basic body.

For selected surface areas of 0 739×0 736 mm$^2$, the average roughness S$_a$ and the Peak to Valley Height S$_t$ were determined among several others roughness parameters. To this purpose, pictures of the surface were taken using a confocal white light microscope (Nanosurf AG, Switzerland). For calculating the roughness parameters, a "moving average" Gaussian filter having a cut-off wavelength of 30 μm (micrometer) (x=31 μm, y=30 μm; 20×19 pixels) was applied. Determination of the roughness parameters was carried out by means of a KFL-analysis (software WinSAM; University of Erlangen).

For the selected areas, the average roughness S$_a$ determined was in the range of about 0.60 μm (micrometer) to about 0.85 μm (micrometer) and the Peak to Valley Height was about S$_t$ 3.5 μm (micrometer) to about 6.0 μm (micrometer). These values are however in no way to be understood in a restrictive manner, as completely different values are thinkable for a surface obtained according to the present invention.

The invention claimed is:

1. A process for preparing a ceramic body having a surface roughness, the process comprising:
depositing on a surface of a ceramic basic body separate agglomerates comprising at least two ceramic particles and a binder by projecting the agglomerates towards the ceramic basic body,
wherein:
the agglomerates deform when impacting on the ceramic basic body such that a contact area between the agglomerates and the ceramic basic body is augmented during impacting; and
the binder binds the ceramic particles together and is present in the agglomerates after their deposition.

2. The process according to claim 1, wherein the agglomerates are projected towards the ceramic basic body by a carrier gas stream.

3. The process according to claim 1, wherein a breaking load of the agglomerates to be projected is in a range of 1 to 7 mN.

4. The process according to claim 1, wherein a mean specific breaking strength of the agglomerates to be projected is in a range of 0.4 to 1.5 MPa.

5. The process according claim 1, wherein the agglomerates have an average diameter ranging from 20 μm to 100 μm.

6. The process according to claim 1, wherein a ceramic material of the ceramic particles is identical to a ceramic material of the ceramic basic body.

7. The process according to claim 1, wherein the agglomerates are projected towards the ceramic basic body by a sand-blasting apparatus.

8. The process according to claim 1, wherein the agglomerates further comprise a pressing agent.

9. The process according to claim 1, further comprising:
forming a green basic body comprising particles of a ceramic material and a binder, said particles and said binder being independent respectively from the ceramic particles and the binder of the agglomerates,
forming a brown basic body by removing the binder from the green basic body, and
forming the ceramic body by sintering the brown basic body.

10. The process according to claim 9, wherein the agglomerates are deposited on a surface of the green basic body.

11. The process according to claim 9, wherein the agglomerates comprise particles of yttriumoxide-stabilized zirconia.

12. The process according to claim 9, wherein a composition of the agglomerates is identical to a composition of the green basic body.

13. The process according to claim 9, further comprising thermal post-processing the ceramic body.

14. A ceramic body obtained by the process according to claim 1.

15. An implant comprising the ceramic body obtained by the process of claim 1.

16. The implant according to claim 15, wherein the implant is a dental implant.

17. The process according to claim 3, wherein the breaking load is in a range of 3 to 5 mN.

18. The process according to claim 4, wherein the mean specific breaking strength is in a range of 0.8 to 1.2 MPa.

19. The process according to claim 5, wherein the average diameter ranges from 50 μm to 70 μm.

20. The process according to claim 1, further comprising cooling the agglomerates immediately prior to the depositing of the agglomerates on the surface of the ceramic basic body to prevent an organic fraction of the agglomerates from melting.

* * * * *